United States Patent [19]

Silvenis et al.

[11] Patent Number: 4,759,501
[45] Date of Patent: Jul. 26, 1988

[54] FRAGRANCE DISPENSING SYSTEM AND PROCESS

[75] Inventors: Scott A. Silvenis, Mauldin; Daniel C. Wilson, Taylors, both of S.C.

[73] Assignee: The Dow Chemical Company, Midland, Mich.

[21] Appl. No.: 97,300

[22] Filed: Sep. 14, 1987

Related U.S. Application Data

[63] Continuation of Ser. No. 866,045, May 22, 1986, abandoned.

[51] Int. Cl.⁴ .................................................. A61L 9/04
[52] U.S. Cl. ........................................ 239/6; 239/34; 239/289; 239/326
[58] Field of Search ............................. 239/34, 53–59, 239/289, 326, 6

[56] References Cited

U.S. PATENT DOCUMENTS

| 2,481,296 | 9/1949 | Dupuy | 239/59 X |
| 3,330,481 | 7/1967 | Dearling | 239/326 X |
| 3,964,684 | 6/1976 | Schimanski | 239/56 |
| 3,972,473 | 8/1976 | Harrison | 239/326 X |
| 4,084,732 | 4/1978 | Dearling | 239/34 X |
| 4,258,004 | 3/1981 | Valenzona et al. | 239/57 X |
| 4,341,348 | 7/1982 | Dearling | 239/326 X |
| 4,361,279 | 11/1982 | Beacham | 239/56 |
| 4,549,693 | 10/1985 | Barlics | 239/55 X |

Primary Examiner—Andres Kashnikow
Assistant Examiner—Mary Beth O. Jones

[57] ABSTRACT

Fragrance dispensing system and process are provided by separately utilizable dispensing apparatus and a source of fragrant dispersant. The dispensing apparatus is charged and recharged by use of the source of aerosol dispersant.

22 Claims, 7 Drawing Sheets

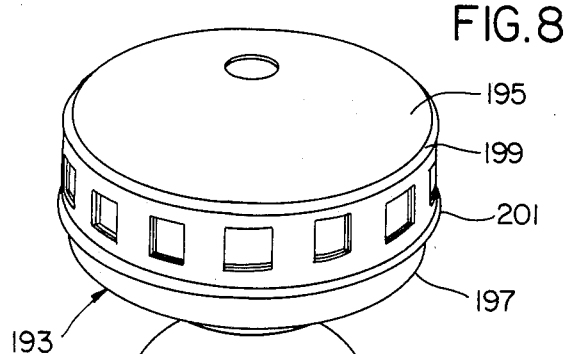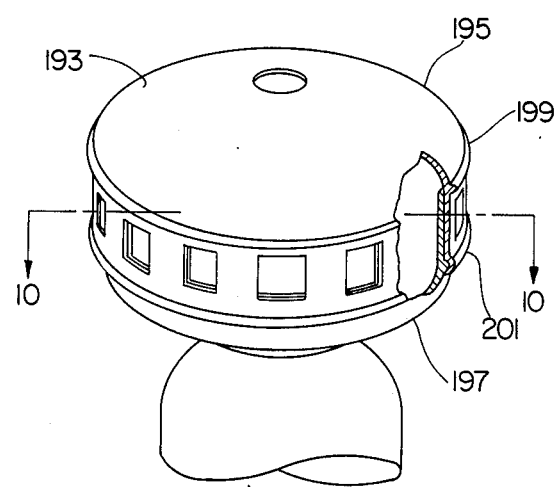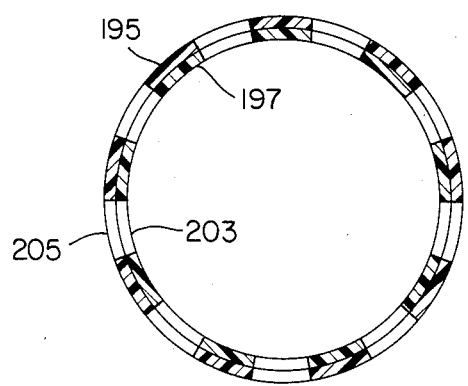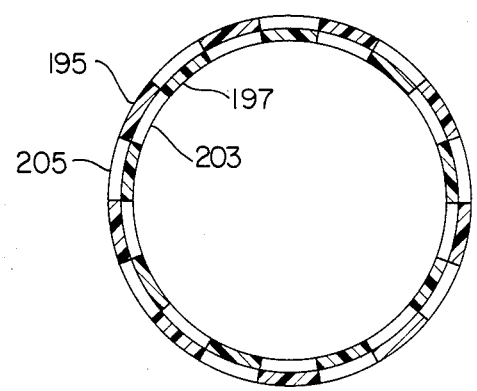

FRAGRANCE DISPENSING SYSTEM AND PROCESS

This application is a continuation of application Ser. No. 866,045, filed 5/22/86, now abandoned.

BACKGROUND OF THE INVENTION

This invention relates generally to the art of fragrance dispensing and more particularly to a novel dispensing system, including both an aerosol dispersant container as well as a rechargeable evaporator device associated therewith.

Various prior art devices have been devised with the overall purpose of disseminating fragrances of one sort or another into the atmosphere. Such fragrances may be in the nature of perfumes or in the nature of insecticides or other volatile repellents. Frequently such volatile substances emanate from a stationary source such as a blotter or absorbant. Examples of such type dispersers or sprayers are described in U.S. Pat. No. 2,760,822 to Boris et al, U.S. Pat. No. 3,964,684 to Schimanski, U.S. Pat. No. 4,361,279 to Beacham, and U.S. Pat. No. 4,258,004 to Valenzona, et al.

Various devices have been envisoned to be associated with aerosol spray devices. One such device is described in U.S. Pat. No. 3,972,473 to Harrison. A variety of devices are described in a series of patents to Dearling wherein an aerosol device is utilized to contain a source of volatile fragrant material for utilization within a sorptive material. Such devices are described in U.S. Pat. Nos. 3,330,481, 4,084,732 and 4,341,348.

U.S. Pat. No. 4,526,320 to von Phillipp et al describes an evaporator device having plural source of fragrance within a housing supporting the fragrance containers as well as sorptive material.

While the above prior art devices are effective for disseminating volatile fragrant materials, a need continues to exist for devices with greater versatility and flexibility.

SUMMARY OF THE INVENTION

It is thus an object of this invention to provide a novel fragrance dispensing apparatus.

It is a further object of this invention to provide such a fragrance dispensing apparatus which is capable of recharging.

It is a further and more particular object of this invention to provide a process for recharging such a fragrance dispensing apparatus.

It is a still further and more particular object of this invention to provide a fragrance dispensing system to include both a dispensing apparatus as well as an aerosol spray.

These as well as other objects are accomplished by a fragrance dispensing system formed of two concaved cups matingly engaged to define a housing for retention therein of a generally planar sorptive material. One of the concaved cups defines a receptacle for receiving an outlet of an aerosol dispersant container so as to permit charging of the sorptive material with the dispersant. The apparatus and aerosol dispersant container may be packaged together to form a fragrance dispensing system.

BRIEF DESCRIPTION OF THE DRAWINGS

FIG. 8 is a perspective view of yet another embodiment in accordance with this invention.

FIG. 9 is a view similar to a portion of FIG. 8 illustrating yet another embodiment in accordance with this invention.

FIGS. 10A and 10B are alternative cross-sectional views along the line 10—10 of FIG. 9.

DETAILED DESCRIPTION

In accordance with this invention it has been found that a fragrance dispensing system may be provided which permits a fragrance dispensing apparatus to be charged and recharged by an aerosol dispersant container and which also permits the aerosol dispersant container to be used independently as a source of fragrance-bearine material. It has additionally been found that the fragrance dispensing apparatus may be charged and positioned at desired locations and recharged for continued use at such remote locations. It has been further found that such apparatus and aerosol dispersant container may be packaged together to form a fragrance dispensing system. Various other advantages and features will become apparent from a reading of the following description given with reference to the various figures of drawing.

Figure 1:
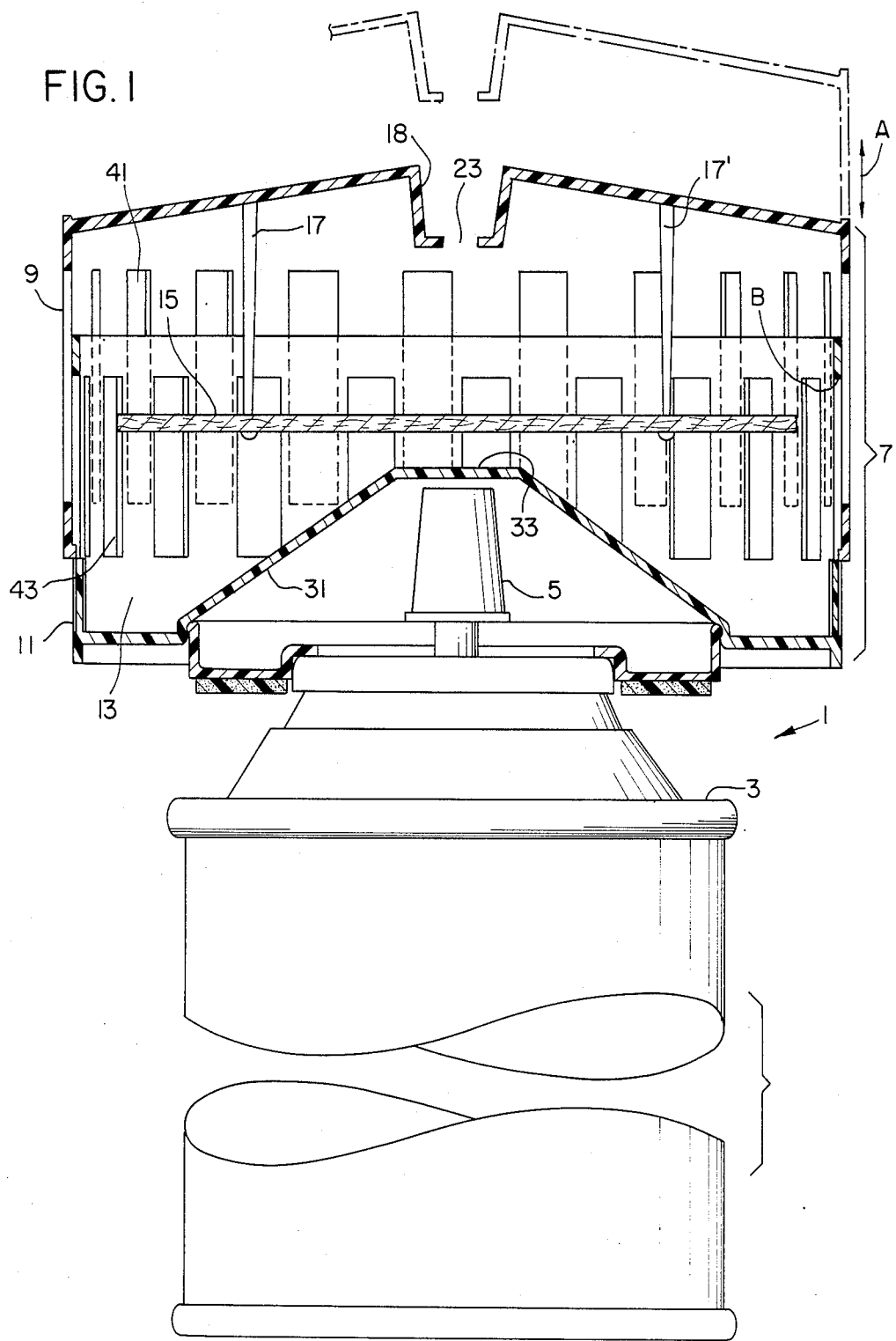
FIG. 1 of the drawings illustrates in cross section a fragrance dispensing system in accordance with this invention.

FIG. 1 of the drawings illustrates an embodiment of the fragrance dispensing system 1 in accordance with this invention. The system comprises a source 3 of aerosol dispersant having an outlet 5. Outlet 5 comprises a valve not shown which is activated to release dispersant by either depression or lateral deflection thereof. The source of dispersant 3 is useful independently as a source of fragrance by lateral deflection of outlet 5.

The fragrance dispensing system additionally comprises a fragrance dispensing apparatus 7 shown in association with dispersant source 3. As illustrated in FIG. 1 the dispensing system 1 is illustrated as a packaged product.

The fragrance dispensing apparatus 7 is illustrated in FIG. 1 in an inverted position from its normal charging position since it is illustrated in its packaged state. Utilization of the apparatus 7 will become apparent from the description below.

The fragrance dispensing apparatus 7 is formed of two concaved cups 9 and 11 which are matingly engaged such that their adjoining concavities form a housing 13. Contained within housing 13 is a generally planar sorptive material 15. Sorptive material 15 is of any of the conventionally utilized materials such as blotter paper which sorb, i.e., adsorb and/or absorb fragrant material for the purpose of dispersing the fragrance into the surrounding atmosphere. Planar sorptive material 15 is supported by one of the concaved cups as by support means such as 17 and 17'.

Figure 2:
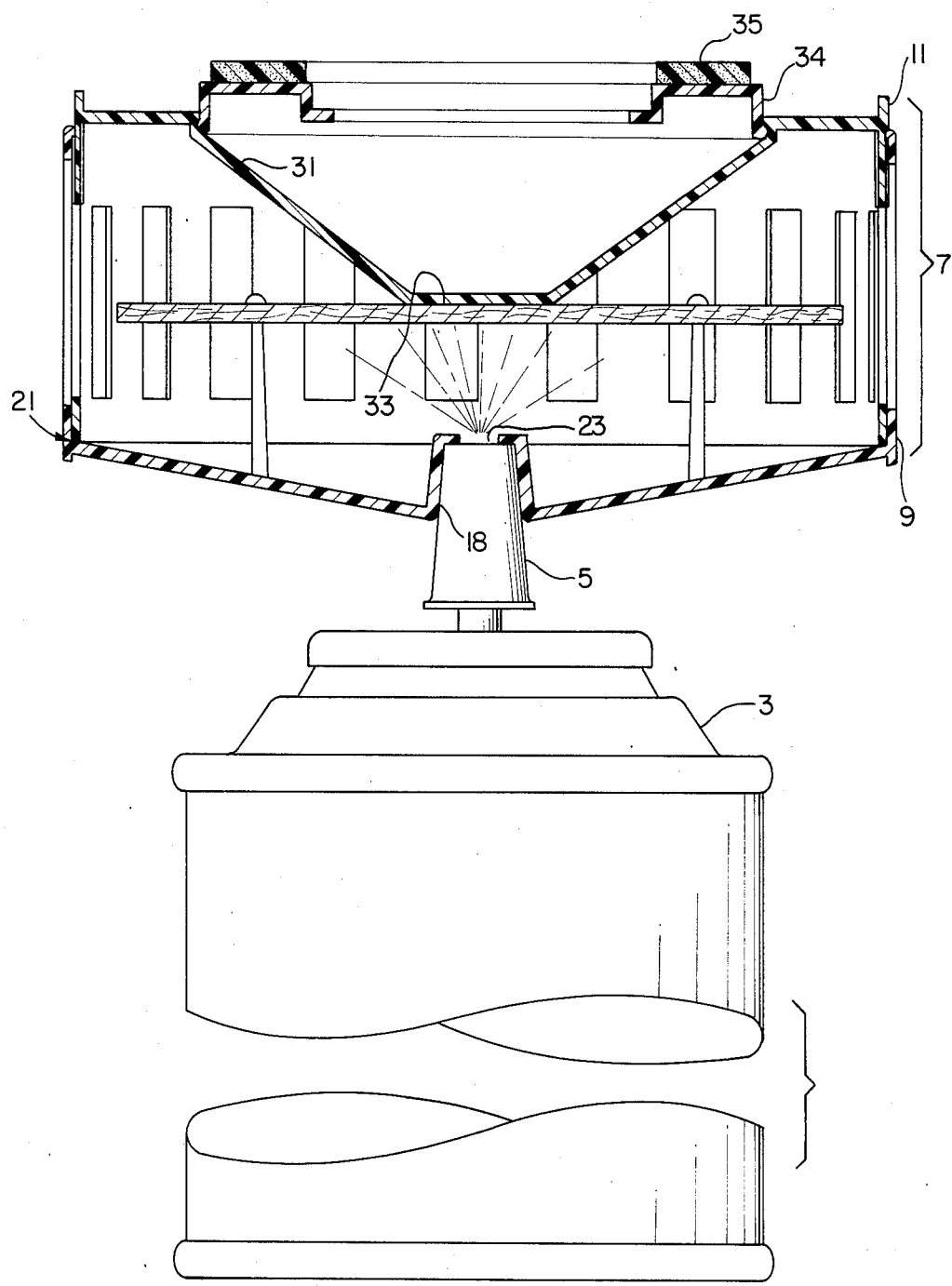
FIG. 2 of the drawings is similar to FIG. 1 but with a portion of the apparatus reversed to illustrate the charging process of this invention.

It should be noted that sorptive material 15 is charged by the technique illustrated in FIG. 2. Referring to FIG. 2 of the drawings it is seen that apparatus 7 is illustrated in the position inverted from that in FIG. 1 with outlet 5 positioned within receptacle 18 defined by concaved cup 9. It should also be noted that concaved cup 9 forms a sleeve about concaved cup 11 such that upon depression of the concaved cup 11 toward source 3, cup 11 moves until that movement is stopped by means such as 21. At this point outlet 5 is depressed, releasing dispersant through orifice 23 where dispersant moves in a direction generally perpendicular to the plane of planar sorbent 15.

It should be noted that upon charging sorbent 15 significant force is released from an aerosol container such as that through outlet 5. In order to reinforce sorptive material 15, which is frequently fragile, concaved cup 11 defines a receptacle 31 which receives and nests with dispersant source 3 when in the packaged state, FIG. 1, but which also when in the charging state, FIG. 2, moves to a position on the opposite side of receptacle 31 as at 33 to back and reinforce sorptive material 15 so as to prevent any dislodgement or distortion thereof during the charging process. It should be noted that only a single motion is required for both positioning and charging apparatus 7 on and by source 3. After charging in the manner illustrated and described with respect to FIG. 2, the apparatus 7 may be positioned for permitting fragrance dissemination in the manner set forth below.

Apparatus 7 is provided with an adapter 34 having a pressure sensitive adhesive 35 thereon at a point generally adjacent to receptacle 31 in order to permit the entire apparatus to be adhesively positioned at desired locations. Such locations may be within trash containers, bathrooms, closets, or even automobiles. Preferably, adapter 34 is a separate structure which snap-fits into receptacle 31. This allows for removal of the apparatus 7 from the adhesively attached position while leaving the adapter so located. This allows for recharging of the apparatus 7 in tight quarters without having to disturb the adhesive attachment.

The amount of dispersant disseminated to the atmosphere may be variably controlled in accordance with this invention. Referring again to FIG. 1 of the drawings it is seen that concaved cup 9 has a plurality of windows illustrated as at 41 while concaved cup 11 also has a plurality of windows illustrated as at 43. Windows 41 and 43 may be superimposed upon one another as is generally depicted in FIG. 2 of the drawings or may be positioned in an unregistered state by rotating concaved cups 9 and 11 with respect to one another. Additionally, since concaved cup 9 forms a sleeve about concaved cup 11 such that the relative longitudinal movement thereof generates a varying amount of space through windows 41 and 43 as illustrated by arrow "A", FIG. 1. Such movement of concaved cups also varies the size of housing 13 defined by the respective concavities.

It is generally seen that the apparatus 7 may be recharged at any particular desired time by merely placing outlet 5 within receptacle 18 and depressing outlet 5. It is further seen that source 3 may be used independently of apparatus 7 to provide fragrance wherever desired.

Figure 3:
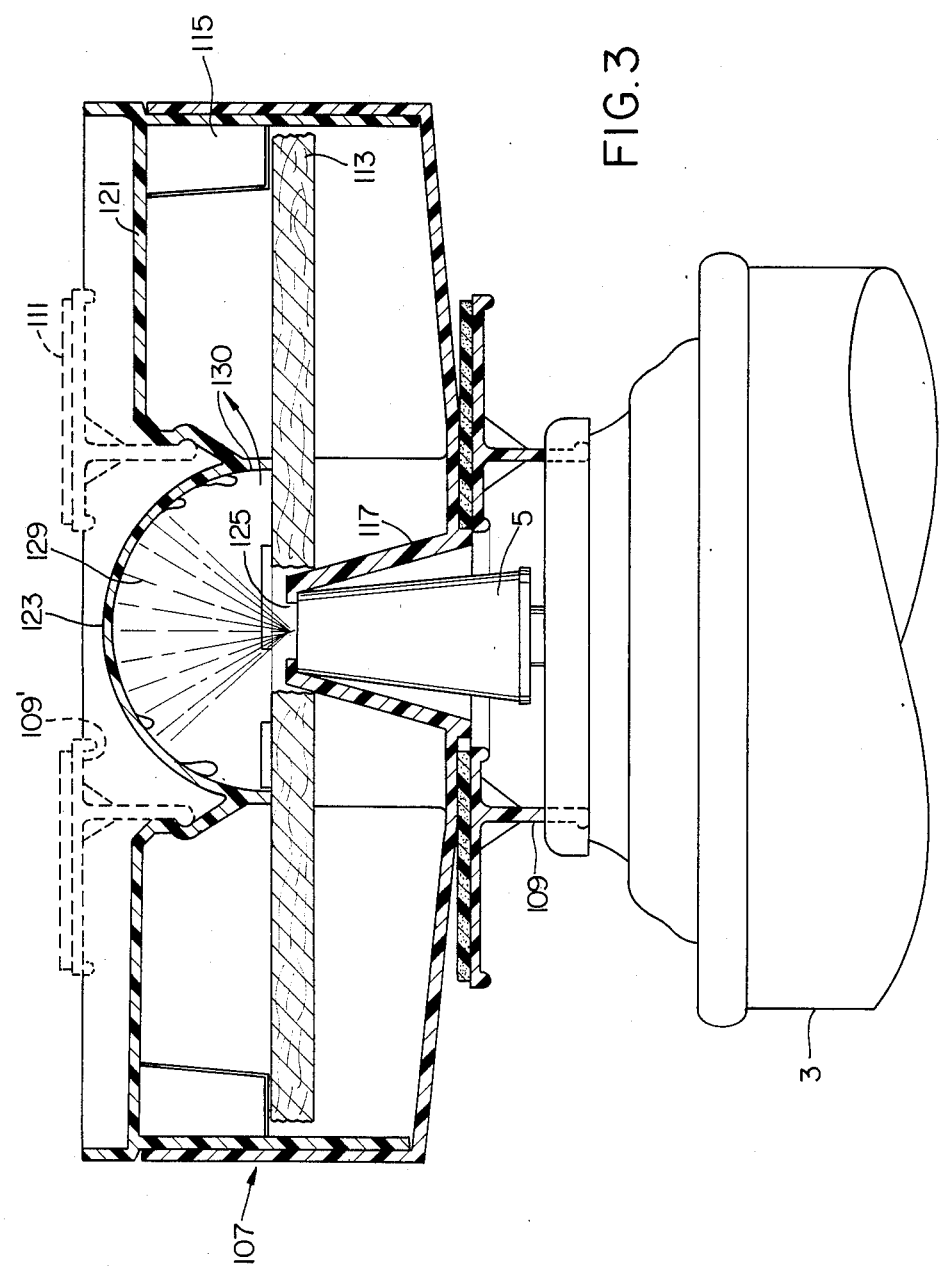
FIG. 3 of the drawings illustrates in cross section an additional embodiment of this invention.

An additional embodiment of the apparatus 107 in accordance with this invention is illustrated in FIG. 3 of the drawings. As illustrated therein a source 3 mates with apparatus 107 having an adapter 109 positioning apparatus 107 for the packaging position. As illustrated in phantom, adapter 109' may be used to locate apparatus 107 at desired locations with pressure sensitive adhesive 111.

Within this embodiment sorptive material 113 is positioned within apparatus 107 by ledge means 115.

Within the FIG. 3 embodiment receptacle 117 passes through sorptive material 113 and generally receives outlet 5 for purposes of charging by the technique described below.

Upper concaved cup 121 is formed with a generally cupped-shaped shroud 123 generally concentrically positioned above orifice 125 of receptacle 117 for receipt of spray from nozzle 5. As is illustrated and is readily apparent, in the absence of adapter 109, apparatus 107 may be depressed upon nozzle 5 to cause flow of spray generally indicated at 129 to impinge upon shroud 123 and to generally drop upon sorptive material 113. This configuration assures that all dispersed material 129 will be sorbed within sorptive material 113 rather than lost as may be possible in the absence of protective shroud 123. Shroud 123 may, of course, be of other configurations such as stemmed in the center to prevent splash back toward orifice 125. Suitable venting is provided as indicated by the directional arrow through vent 130.

Figure 4:
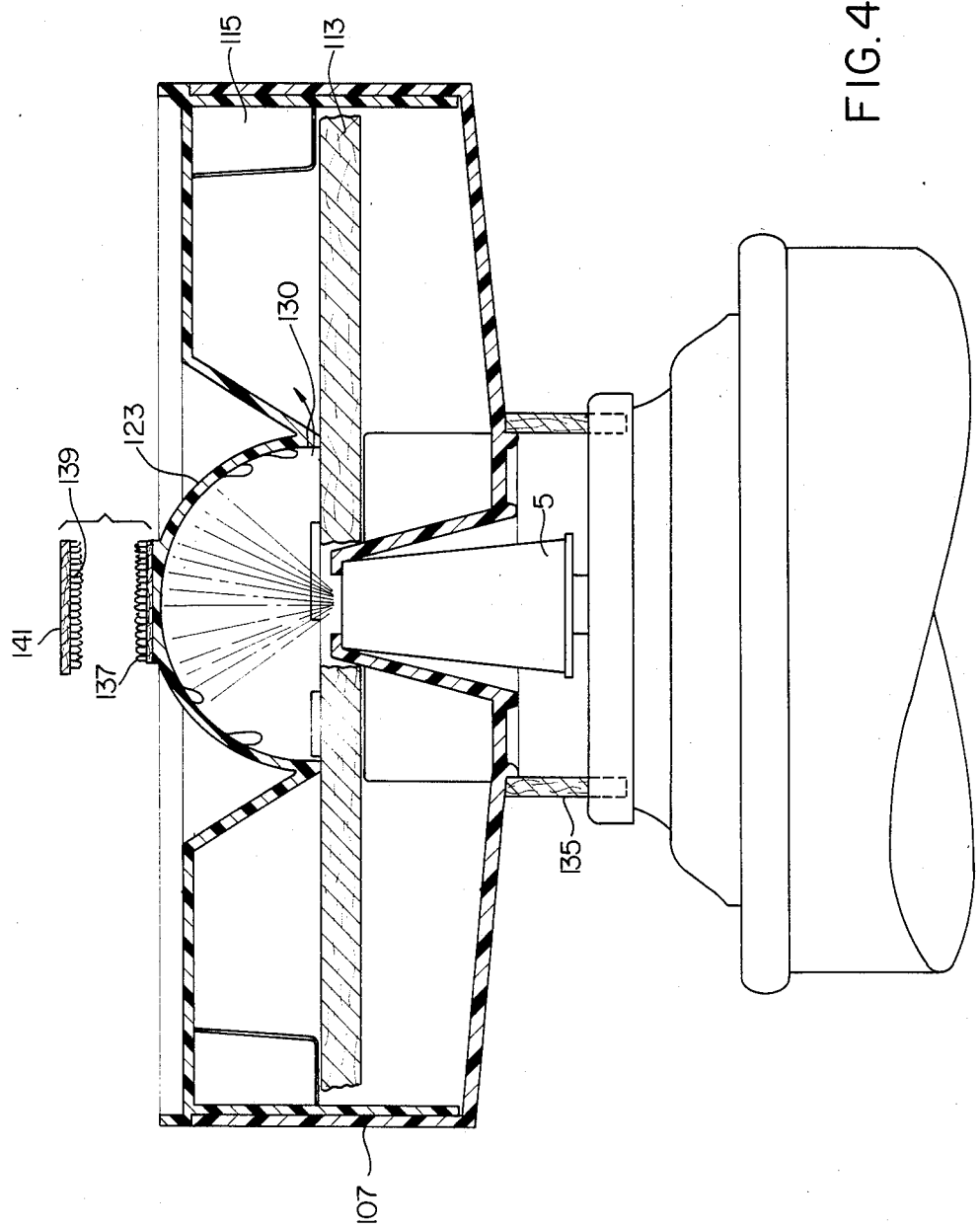
FIG. 4 of the drawings illustrates in cross-section yet a further embodiment in cross section of this invention.

Another embodiment is illustrated in FIG. 4 which is similar to the FIG. 3 embodiment, but wherein adapter 109 has been eliminated and replaced by a temporary sleeve 135 which is used solely for purposes of packaging as illustrated in the FIG. 4 embodiment. The FIG. 4 embodiment is charged in the same manner as the FIG. 3 embodiment after removal of temporary sleeve 135. Apparatus 107 in the FIG. 4 embodiment is positioned at remote locations by means of velcro 137 which is attached to mating velcro 139 having pressure sensitive adhesive 141 attached thereto for such remote positioning.

Figure 5:
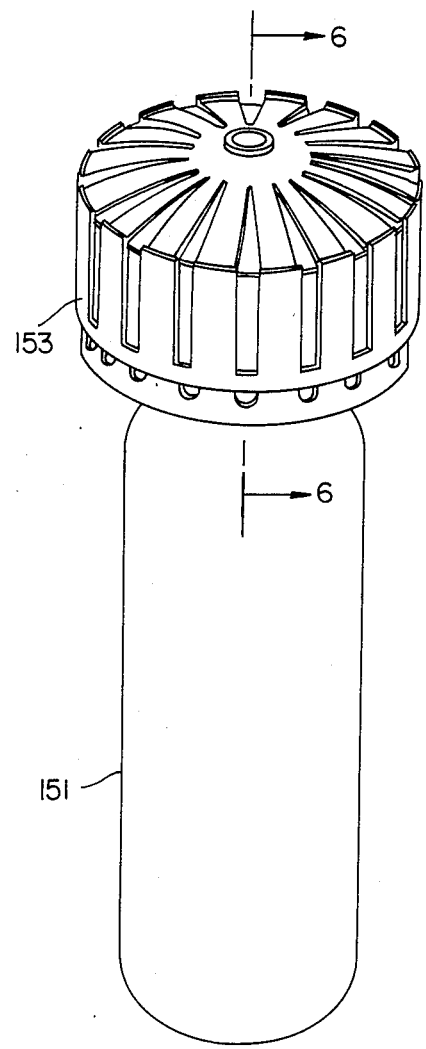
FIG. 5 is a perspective view of yet an additional embodiment of this invention.

FIG. 5 of the drawings illustrates yet another embodiment of the invention wherein an aerosol container 151 has a fragrance dispensing apparatus 153 positioned on top thereof for packaging purposes. Apparatus 153 may be best viewed in FIG. 6 which is a view along the line 6—6 of FIG. 5. It is seen that apparatus 153 is formed of an upper concaved cup 155 and a lower concaved cup 157 telescopically received within concaved cup 155. In this embodiment sorptive material 159 is positioned within cup 157 by location above receptacle 161. Receptacle 161 additionally serves the purpose of receiving an outlet of aerosol container 151. In the manner illustrated, concaved cups 155 and 157 are positioned for rotation and telescoping so as to regulate atmospheric exposure due to the alignment or lack thereof of windows 163 and 165. Orifice 167 provides means for charging sorptive material 159 in the manner previously described. It is, of course, understood that apparatus 153 may be provided so as to regulate venting by either rotation or telescoping so as to simplify the construction thereof.

Figure 6:
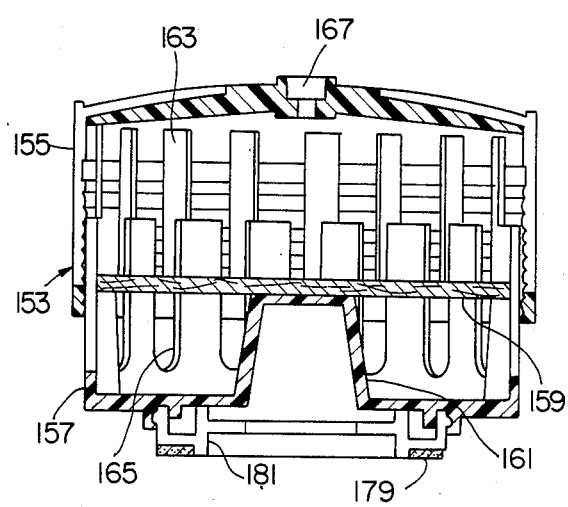
FIG. 6 is a view along the line 6—6 of FIG. 5.
Figure 7:
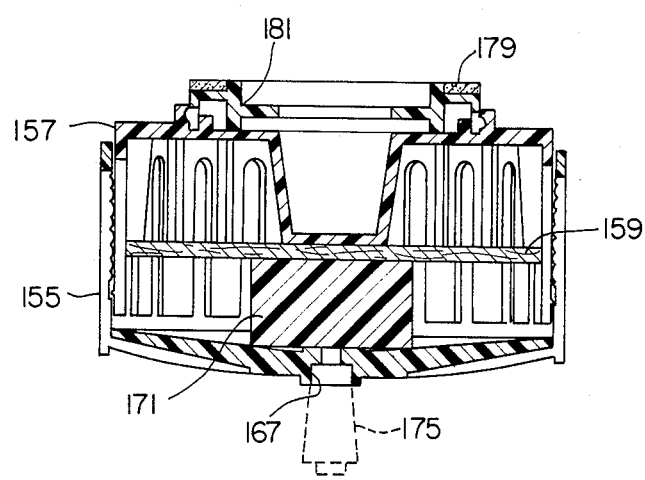
FIG. 7 is a view similar to FIG. 6 in cross-section of an additional embodiment in accordance with this invention.

FIG. 7 of the drawings is a view similar to FIG. 6 illustrating yet an additional aspect of this invention. The FIG. 7 view is inverted from the view illustrated in FIG. 6 and is additionally provided with an additional sorbent material 171 in direct communication with orifice 167. The purpose of additional sorbent material 171 is to directly absorb fragrant material from aerosol outlet 175 and directly transmit such material to sorptive material 159. This eliminates any likelihood of flyaway material which may be particularly undesireable in some circumstances.

The FIGS. 5 through 7 embodiments are also provided with means for attachment such as pressure sensitive adhesive 179 and an adapter 181 for mating with aerosol container 151.

FIGS. 8 through 10 relate to additional embodiments illustrating variations in the means for regulating exposure of the sorptive material to the atmosphere. FIG. 8 illustrates a container 191 having an apparatus 193 thereon in accordance with this invention. The apparatus 193 is adapted for regulating exposure by rotation of upper section 195 with respect to lower section 197. To aid in rotation, beads 199 and 201 are provided to assist in gripping.

FIG. 9 of the drawings best illustrates this construction in the cutaway view thereof. It is illustrated at FIG. 10A that sections 197 and 195 are aligned so as to permit complete registry of windows 203 and 205. FIG. 10B, however, illustrates windows 205 and 203 in a nonregistered state to foreclose communication between the sorptive material and surrounding atmosphere. Windows 10A and 10B may be of other configurations for ornamental purposes. Sloped or toothed windows, for example, present a unique appearance upon rotation of the respective parts.

Figure 11:
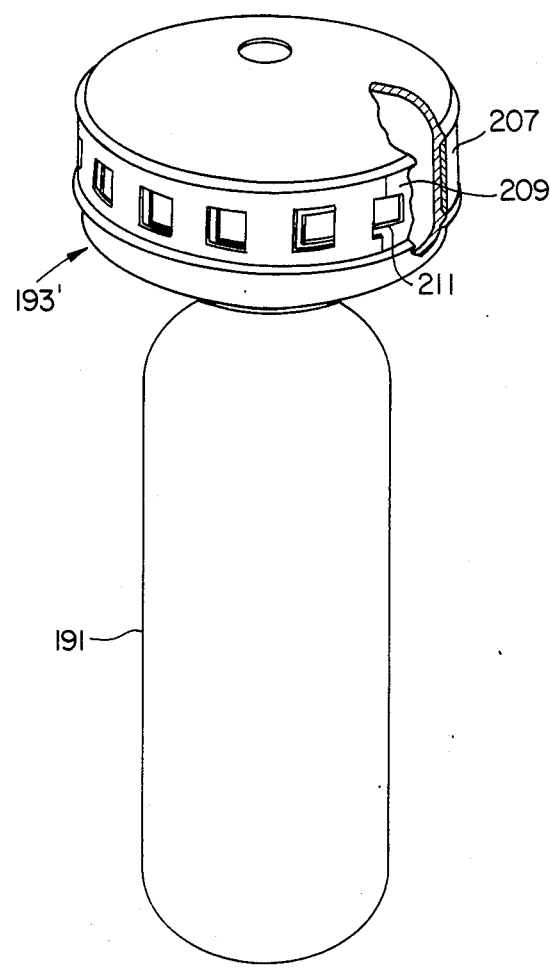
FIG. 11 is yet another perspective view of the embodiment of this invention.

FIG. 11 of the drawings illustrates yet another embodiment wherein apparatus 193 is of unitary construction so that the upper and lower sections thereof do not move with respect to one another. A sleeve 207, however, is provided which rotates with respect to the apparatus 193 such that its windows 209 may be either registered or nonregistered with windows 211 of apparatus 193.

It is thus seen that this invention provides a novel fragrance dispensing system which includes independently utilizable sources of dispersant as well as an apparatus for dispensing fragrance. As many variations will become apparent from the above description which is exemplary in nature such variations are embodied within the spirit and scope of the subject invention as defined by the following appended claims:

What is claimed is:
1. A fragrance dispensing apparatus, comprising:
   a first concaved cup;
   a second concaved cup, said first and second concaved cups being matingly engaged whereby a housing is defined by the concavities of each said concaved cups;
   a generally planar sorptive material generally centrally disposed within said housing and supported by one of said concaved cups said planar sorptive material dividing said housing into two sections adjacent each concaved cup;
   one of said concaved cups defining a first receptacle to receive an outlet of an aerosol dispersant container and an orifice in communication with said first receptacle, said first receptacle and orifice being arranged to disperse aerosol from said container in a direction generally perpendicular to the plane of said planar sorptive material for the charging and recharging thereof with fragrant material.

2. The apparatus according to claim 1 wherein said first and second concaved cups matingly engage by one of said cups forming a sleeve about the other of said cups.

3. The apparatus according to claim 2 wherein said concaved cups are adjustably engaged to permit varying the size of said housing.

4. The apparatus according to claim 2 wherein said concaved cups define windows with the windows of said concaved cup forming said sleeve being superimposeable over the windows of said other concaved cup.

5. The apparatus according to claim 4 wherein said concaved cups are rotatble one within the other whereby said windows may be registered in said superimposed state or unregistered to preclude gaseous communication through said windows.

6. The apparatus according to claim 1 wherein the other of said concaved cups not defining said first receptacle defines a second receptacle to nestingly receive said aerosol dispersant container and form a package therewith.

7. The apparatus according to claim 6 wherein said second receptacle is adapted to receive said container on the exterior of said other concaved cup with the interior of said other cup supporting said planar sorptive material inside said housing during the charging thereof through said orifice.

8. The apparatus according to claim 6 further including an adhesive disposed about said second receptacle for adhering said apparatus to a surface.

9. The apparatus according to claim 8 wherein said adhesive is a pressure sensitive adhesive.

10. The apparatus according to claim 8 wherein said adhesive is a velcro adherent.

11. The apparatus according to claim 1 wherein one of said concaved cups defines a shroud opposite said first receptacle and wherein said planar sorptive material defines an orifice within the central portion thereof whereby dispersant from said aerosol dispersant container passes through said orifice and contacts said shroud for dispensing to said sorptive material.

12. The apparatus according to claim 1 further comprising an adhesive on one of said concaved cups for adhering said apparatus to a surface.

13. A fragrance dispensing system comprising:
   an aerosol dispersant container having an outlet;
   a first concaved cup;
   a second concaved cup, said first and second concaved cups being matingly engaged whereby a housing is defined by the concavities of each of said concaved cups;
   a generally planar sorptive material generally centrally disposed within said housing and supported by one of said concaved cups said planar sorptive material dividing said housing into two sections adjacent each concaved cup;
   one of said concaved cups defining a first receptacle to receive said outlet of said aerosol dispersant container and an orifice in communication with said receptacle, said first receptacle and orifice being arranged to disperse aerosol from the outlet of said aerosol dispersant container in a direction generally perpendicular to the plane of said planar sorptive material for charging and recharging thereof with fragrant material;
   the other of said concaved cups not defining said first receptacle defining a second receptacle to nest with said aerosol diapersant container and form a package therewith.

14. The system according to claim 13 wherein said first and second concaved cups together said planar sorptive material may be charged with said aerosol dispersant and independently used as a fragrance source and wherein said aerosol dispersant container may be independently used to disperse fragrance through the outlet thereof.

15. A process for charging a fragrance dispensing device, comprising the steps of:
providing a dispersant container having a dispersant therein;
providing a fragrance dispensing apparatus comprising:
a first concaved cup;
a second concaved cup, said first and second concaved cups being matingly engaged whereby a housing is defined by the concavities of each said concave cups;
a generally planar sorptive material generally centrally disposed within said housing and supported by one of said concaved cups;
one of said concaved cups defining a first receptacle exterior to said housing to receive an outlet of said dispersant container and an orifice in communication with said first receptacle, said first receptacle and orifice being arranged to disperse contents from said container in a direction generally perpendicular to the plane of said planar sorptive material for charging and recharging thereof with fragrant material;
placing the outlet of said dispersant container within said first receptacle exterior to said housing;
moving said apparatus toward said container to open the valve thereof and release dispersant through said orifice to charge said sorptive material.

16. A fragrance dispensing apparatus, comprising:
a first concaved cup;
a second concaved cup, said first and second concaved cups being matingly engaged whereby a housing is defined by the concavities of each said concaved cups;
a generally planar sorptive material generally centrally disposed within said housing and supported by one of said concaved cups;
one of said concaved cups defining a first receptacle to receive an outlet of an aerosol dispersant container and an orifice in communication with said first receptacle, said first receptacle and orifice being arranged to disperse aerosol from said container in a direction generally perpendicular to the plane of said planar sorptive material for the charging and recharging thereof with fragrant material;
the other of said concaved cups defining a second receptacle to nestingly received said aerosol dispersant container and form a package therewith; and
an adhesive disposed about said second receptacle for adhering said apparatus to a surface.

17. The apparatus according to claim 16 wherein said adhesive is a pressure sensitive adhesive.

18. The apparatus according to claim 16 wherein said adhesive is a velcro adherent.

19. A dispersant dispensing apparatus, comprising:
a first concaved cup;
a second concaved cup, said first and second concaved cups being matingly engaged whereby a housing is defined by the concavities of each said concaved cups;
a generally planar sorptive material generally centrally disposed within said housing and supported by one of said concaved cups said planar sorptive material dividing said housing into two (2) sections adjacent each concaved cup;
one of said concaved cups defining a first receptacle to receive an outlet of a dispersant container and an orifice in communication with said first receptacle, said first receptacle and orifice being arranged to disperse dispersant from said container in a direction generally perpendicular to the plane of said planar sorptive material for the charging and recharging thereof with said dispersant.

20. A dispersant dispensing system comprising:
a dispersant container having an outlet;
a first concaved cup;
a second concaved cup, said first and second concaved cups being matingly engaged whereby a housing is defined by the concavities of each of said concaved cups;
a generally planar sorptive material generally centrally disposed within said housing and supported by one of said concaved cups said planar sorptive material dividing said housing into two (2) sections adjacent each concaved cup;
one of said concaved cups defining a first receptacle to receive said outlet of said dispersant container and an orifice in communication with said receptacle, said first receptable and orifice being arranged to disperse dispersant from the outlet of said dispersant container in a direction generally perpendicular to the plane of said planar sorptive material for charging and recharging thereof with dispersant material;
the other of said concaved cups not defining said first receptacle defining a second receptacle to nest with said dispersant container and form a package therewith.

21. A process for charging a dispersant dispensing device, comprising the steps of:
providing a dispersant container having a dispersant therein;
providing a dispensing apparatus comprising:
a first concaved cup;
a second concaved cup, said first and second concaved cups being matingly engaged whereby a housing is defined by the concavities of each said concave cups;
a generally planar sorptive material generally centrally disposed within said housing and supported by one of said concaved cups;
one of said concaved cups defining a first receptacle exterior to said housing to receive an outlet of said dispersant container and an orifice in communication with said first receptacle, said first receptacle and orifice being arranged to disperse contents from said container in a direction generally perpendicular to the plane of said planar sorptive material for charging and recharging thereof with dispersant material;
placing the outlet of said dispersant container within said first receptacle exterior to said housing; and, releasing dispersant through said orifice to charge said sorptive material.

22. A dispersant dispensing apparatus, comprising:

a first concaved cup;

a second concaved cup, said first and second concaved cups being matingly engaged whereby a housing is defined by the concavities of each said concaved cups;

a generally planar sorptive material generally centrally disposed within said housing and supported by one of said concaved cups;

one of said concaved cups defining a first receptacle to receive an outlet of a dispersant container and an orifice in communication with said first receptacle, said first receptacle and orifice being arranged to disperse dispersant from said container in a direction generally perpendicular to the plane of said planar sorptive material for the charging and recharging thereof with dispersant;

the other of said concaved cups defining a second receptacle to nestingly received said dispersant container and form a package therewith; and, an adhesive disposed about said second receptacle for adhering said apparatus to a surface.

* * * * *